United States Patent
Johs et al.

(10) Patent No.: US 7,362,435 B1
(45) Date of Patent: Apr. 22, 2008

(54) METHOD OF DETERMINING INITIAL THICKNESS VALUE FOR SAMPLE SURFACE LAYER, AND USE OF SPLINES FOR FITTING ELLIPSOMETRIC DATA

(75) Inventors: Blaine D. Johs, Lincoln, NE (US); Jeffrey S. Hale, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 310 days.

(21) Appl. No.: 11/326,060

(22) Filed: Jan. 5, 2006

Related U.S. Application Data

(60) Provisional application No. 60/642,493, filed on Jan. 10, 2005.

(51) Int. Cl.
*G01J 4/00* (2006.01)
(52) U.S. Cl. .................. 356/369; 356/630; 250/559.27
(58) Field of Classification Search ................ 356/369, 356/630; 250/559.27
See application file for complete search history.

(56) References Cited

U.S. PATENT DOCUMENTS

| | | | | |
|---|---|---|---|---|
| 4,999,509 | A | | 3/1991 | Wada et al. ................ 250/560 |
| 5,889,592 | A | | 3/1999 | Zawaideh .................... 356/357 |
| 5,953,446 | A | | 9/1999 | Opsal et al. ................ 382/141 |
| 6,278,519 | B1 | * | 8/2001 | Rosencwaig et al. ........ 356/369 |

OTHER PUBLICATIONS

"Multiple Minima in the Ellipsometric Error Function", Alterovitz & Johs, Thin Solid Films, (1998).
"Simultaneous Measurement of Six layers in a Silicon Insulator Film Stack Using Spectrophotometry and Beam Profile Reflectometry", Lang et al., J. App. Phys., 81(8) (1997).
"Parameter Correlation and Precision in Multiple-Angle Ellipsometry", Bu-Abbud & Bashara, Applied Optics 20 (1981).
"Overview of Variable Angle Spectroscopic Ellipsometry (VASE), Part 1: Basic Theory and Typical Applications", Woollam et al. SPIE Proc CR72 (1999).
"Overview of Variable Angle Spectroscopic Ellipsometry (VASE), Part 1: Basic Theory and Typical Applications", Woollam et al. SPIE Proc CR72 (1999).
"Effective Dielectric Function of Mixtures of Three or More Materials: a Numerical Procedure for Computation", Bosch et al., Surface Science 453 (2000).
"Characterization of Multilayer GaAs/AlGaAs Transistor Structures by Variable Angle Spectroscopic Ellipsometry", Merkle et al., Jap. J. of Appl. Phys. 28, (1989).
"Spectroellipsometric Characterization in Inhomogeneous Films", Tirri et al., SPIE Proc. 794 (1987).
"High Precision UV-Visible-Near-IR Stokes Vector Spectroscopy", Zettler et al., Thin Solid Films, 234 (1993).

* cited by examiner

*Primary Examiner*—Roy M Punnoose
(74) *Attorney, Agent, or Firm*—James D. Welch

(57) ABSTRACT

A method of determining a starting value for thickness of the most influential layer in a mathematical model of a sample for use in a data fitting routine, supplemented by the use of ordinary or B-spline polynomials to represent at least one of the real and imaginary parts of optical constants in the mathematical model.

40 Claims, 1 Drawing Sheet

METHOD OF DETERMINING INITIAL THICKNESS VALUE FOR SAMPLE SURFACE LAYER, AND USE OF SPLINES FOR FITTING ELLIPSOMETRIC DATA

This application Claims Benefit of Provisional Application Ser. No. 60/642,493 Filed Jan. 10, 2005.

TECHNICAL FIELD

The disclosed invention pertains to determining initial and final values for parameters in a mathematical model of a sample which comprises a substrate and at least one thin layer on a surface thereof; and more particularly to an approach for determining an initial thickness for the most influential thin layer, and/or use of polynomials to represent at least one of the real and imaginary parts of optical constants in determining final values for said parameters.

BACKGROUND

The practice of Ellipsometry provides a method to characterize samples which have at least one surface layer thereupon. Values for thickness and optical constants are determined by obtaining ellipsometric data, proposing a mathematical model of the sample and performing a comparison procedure, such as mathematical regression, to evaluate parameters in said mathematical model. Mathematical regression, however, works best when good starting values for parameters in the mathematical model are utilized. This is particularly true for parameters which are more significant than others in the model. One approach to determining starting values is to provide a grid of values and test numerous combinations. This provides utility, but can be tedious and time consuming.

Patents that describe obtaining good initial values are:
U.S. Pat. No. 5,889,592 to Zawaideh which describes simultaneously measuring optical constants and thickness of single and multilayer films. Discussed are use of "Global Optimization Algorithms" to minimize error.
U.S. Pat. No. 4,999,509 to Wada et al. describes the use of global and local optimization methods to determine film thickness of single and multilayer films.
U.S. Pat. No. 5,953,446 to Opsal et al. describes use of genetic algorithms.
U.S. Pat. No. 6,278,519 to Rosenscwaig et al., describes common routines/algorithms used in optical measurements and genetic algorithms to search parameter space.

Papers that concern the topic are:
"Multiple Minima in the Ellisometric Error Function", Alterovitz & Johs, Thin Solid Films, (1998), which describes how to find correct global minima which multiple local minima are present. A Grid Search is described which involves searching a range of possible values for parameters and combinations thereof and results are analyzed by the Levenberg-Marquardt algorithm to identify the smallest Error Function (MSE).
"Simultaneous Measurement of Six layers in a Silicon Insulator Film Stack Using Spectrophotometry and Beam Profile Reflectometry", Lang et al., J. App. Phys., 81(8) (1997). This paper describes a global optimization for a system of up to 12 parameters. The Levenberg-Marquardt algorithm is applied and a best solution is found as a global minimum. A Cauchy dispersion model is used to describe optical constants.
"Parameter Correlation and Precision in Multiple-Angle Ellipsometry", Bu-Abbud & Bashara, Applied Optics 20 (1981). This article describes solutions for desired variables/parameters when many angles of incidence are used. A two step approach is used of doing a Global Search to obtain First Estimates of Parameters, followed by a Detailed Regression.
"Overview of Variable Angle Spectroscopic Ellipsometry (VASE), Part 1: Basic Theory and Typical Applications", Woollam et al. SPIE Proc. CR72 (1999). This article describes use of the Levenberg-Marquardt algorithm along with global-searching to find the correct "global" minimum.
"Overview of Variable Angle Spectroscopic Ellipsometry (VASE), Part 1: Basic Theory and Typical Applications", Woollam et al. SPIE Proc CR72 (1999). This paper discusses detail optical constant parameterization using dispersion models.
"Effective Dielectric Function of Mixtures of Three or More Materials: a Numerical Procedure for Computation", Bosch et al., Surface Science 453 (2000). This article describes applying minimization algorithm techniques applied in Effective Medium Approximation equations.
"Characterization of Multilayer GaAs/AlGaAs Transistor Structures by Variable Angle Spectroscopic Ellipsometry", Merkle et al., Jap. J. of Appl. Phys. 28, (1989). This article describes spanning a large range of parameter values to arrive at good-fit parameters.
"Spectroellipsometric Characterization in Inhomogeneous Films", Tirri et al., SPIE Proc. 794 (1987). This article describes use of global optimization algorithms to find correct "global" minimum. Sensitivity factors and model results are provided.
"High Precision UV-Visible-Near-IR Stokes Vector Spectroscopy", Zettler et al., Thin Solid Films, 234 (1993). This article describes KK consistency applied to Cubic Splines.

Books identified are:
"Numerical Mathematics and Computing" by Cheney and Kincaid, Third Edition, Brooks/Cole Publishing Company, 1994, which describes Splines, and is incorporated by reference herein; and
"Techniques for Characterization of Electrodes and Electrochemical Processes", Varma & Selman, John Wiley & Sons, Chp. 2 "Ellipsometry as in Situ Probe for the Study of Electrode Processes" Mueller.

Even in view of the known prior art, need exists for improved methodology for identifying good starting values for mathematical model equation coefficients when a square error reduction fit is performed to fit the mathematical model to data.

DISCLOSURE OF THE INVENTION

The present invention is, in part, a method of determining an initial thickness of the most influential surface layer in a sample which comprises a substrate and at least one layer on a surface thereof. Said method begins with the steps of:

a) obtaining ellipsometric data over spectroscopic range of wavelengths by causing a spectroscopic polarized beam of electromagnetic radiation to interact with said sample and enter a detector;

b) proposing a mathematical model of said sample including a variable thickness parameter for the most influential surface layer, and an assumed reasonable value of optical constants therefore;

which can be practiced simultaneously or in either order.

(Note, the mathematical model accounts for all layers and the substrate, but all parameters for thickness and optical constants etc., other than the thickness of the most influential layer, are given fixed values).

The method continues by:

c) selecting a first wavelength and determining a list of most influential layer thicknesses for which the mathematical model provides a match to the data at that wavelength, in view of said assumed reasonable values of optical constants for said most influential layer;

d) sequentially testing each thickness for the most influential layer on the list at an additional wavelength to determine the thickness on the list for which the mathematical model provides a match to the ellipsometric data at said additional wavelength.

(Note, step d typically involves determining which thickness on the list provides the best match to the ellipsometric data at a plurality of additional wavelengths. Further, it is noted that a least square error test is typically used to provide guidance as to what values of thickness are correct).

(Note, many samples can be considered to have a substantially transparent most influential layer and the procedure practiced using only a fixed value for a refractive index, rather than both optical constant real and imaginary parts).

Further, a plurality of optical constant values around said reasonable values can be substituted to determine if a better fit for thickness can be achieved as evidenced by a lesser square error value.

Once good fit is achieved at a plurality of wavelengths, a global fit of all model parameters, using all wavelengths, can be performed to better identify thickness and optical constants of said most influential layer.

A preferred form for presenting the ellipsometric data is:
$S = \text{Sin}(2\Psi) \text{Sin}(\Delta)$ vs. thickness;

which often oscillates both negative and positive about a zero, (eg. for a sample with a thick transparent layer). When this approach is used, the thickness list is determined by where S crosses zero on said plot of S vs. thickness. The thicknesses identified are then tested at least one additional wavelength to determine which thickness is correct. It is mentioned that this approach allows said thicknesses to be determined very efficiently by noting thicknesses before and after the thickness at which the S value passes through a zero, as indicated by positive and negative values of S, followed by bisection reduction of the separation between the thicknesses until convergence of S to substantially zero is determined.

It is noted that the ellipsometric data can be presented in a form which oscillates both negative and positive about an average value, instead of a zero value, and the foregoing remains valid, with the terminology "average value" replacing the terminology "zero".

It is also to be understood that other approaches to displaying a plot of a parameter vs. thickness can be elected, such as using a selection from the group:

$C = \text{Sin}(2\Psi) \text{Cos}(\Delta)$;
$N = \text{Cos}(2\Psi)$.

Similarly, any mathematical function which provides oscillatory ellipsometric data presentation, (eg. Trig, Bessel Functions etc.), can be applied in place of S, C, and/or N.

The method typically is applied to a sample for which the mathematical model includes a plurality of surface layers, each of which, except for the most influential layer, is provided fixed starting values for thickness and optical constants.

The method can also involve including parameters in the mathematical model corresponding to surface roughness and composition grading, and testing a plurality of values for at least one selection from the group consisting of:

surface roughness;
composition grading;

to determine if a better fit for thickness can be achieved as evidenced by a lesser square error value.

It is further noted that an approach to globally fitting ellipsometric data over a large range of wavelengths, or equivalent wave number or energy etc., involves point by point fitting. Said approach begins in a region where the ellipsometric data, (eg. e1 or e2 optical constants/dielectric function), is fairly well behaved, and steps in small increments into a region characterized by large fluctuations. This approach can tedious to apply, however, and an alternative would provide benefit.

The present invention then further provides that a method of fitting data comprise the steps of:

a) obtaining ellipsometric data over a spectroscopic range;

b) proposing a mathematical model comprising real and imaginary parts of optical constants as well as layer thicknesses;

c) selecting a subset of said ellipsometric data and evaluating coefficients in polynomials in said mathematical model which are used to represent at least one of the real and imaginary parts of optical constants, as well as other mathematical model parameters;

d) increasing the subset of the data being considered, and using the values obtained in step c as starting values, evaluating values for polynomial coefficients in the mathematical model comprising real and imaginary parts of optical constants, as well other mathematical model parameters in the entire selected subset of data.

The subset of the data being considered can then again be increased, and using the values obtained in step d as starting values, re-evaluating values for parameters in the mathematical model comprising real and imaginary parts of optical constants as well as layer thicknesses. A preferred form of a polynomial form is a cubic or basic spline, however any mathematical function which can fit to optical constants can be applied.

The method of obtaining good starting values for a most influential layer thickness in a sample can be combined with the use of parameterization to fit real and/or imaginary optical constants. Such a method of fitting ellipsometric data to a mathematical model comprises:

A) determining an initial thickness of the most influential surface layer in a sample which comprises a substrate and at least one layer on a surface thereof, by the steps of:

practicing steps a and b in either order or simultaneously:

a) obtaining ellipsometric data over spectroscopic range of wavelengths by causing a spectroscopic polarized beam of electromagnetic radiation to interact with said sample and enter a detector;

b) proposing a mathematical model of said sample including a variable thickness parameter for the most influential surface layer, and an assumed reasonable value of optical constants therefore;

c) selecting a first wavelength and determining a list of most influential layer thicknesses for which the mathematical model provides a match to the data at that wavelength, in view of said assumed reasonable values of optical constants for said most influential layer;

d) sequentially testing each thickness for the most influential layer on the list at least one additional wavelength to determine the thickness on the list for which the mathematical model provides a match to the ellipsometric data at said at least one additional wavelength; and B) utilizing said identified thickness for the most influential layer as a starting value and performing a fitting procedure to better define said most influential layer comprising the step of:

e) selecting a subset of said ellipsometric data and assigning a polynomial to represent at least one of the real and imaginary parts of the optical constants and evaluating coefficients in said polynomial in said mathematical model, as well as re-evaluating said most influential layer thickness by a fitting procedure to said subset of data.

Said method of fitting data can further comprise an additional step of:

f) increasing the subset of the data being considered, and using the values obtained in step c as starting values, evaluating values for polynomial coefficients in the mathematical model which represent at least one of said real and imaginary parts of the optical constants, as well as re-evaluating the thickness of the most influential layer over the entire selected subset of data.

Said method can provide that the thickness on the list which provides a match to the ellipsometric data at a plurality of additional wavelengths.

Said method can also further involve testing a plurality of optical constant values around said reasonable optical constant values to determine if a better fit for thickness can be achieved as evidenced by a lesser square error value, said optical constant values being varied for at least one optical constant selected from the group consisting of:
the real; and
the imaginary;

part.

A global fit at all wavelengths can also be performed to better identify thickness and optical constant values of said most influential layer.

Said method can provide that the ellipsometric data be presented in the form of:

S=Sin(2Ψ) Sin(Δ) vs. thickness;

which oscillates both negative and positive about a zero or average value at said first wavelength wherein the list of thicknesses is determined by noting a plurality of locations where the S value crosses said zero. Further, the thicknesses can be determined by noting thicknesses before and after the thickness at which the S value passes through a zero, as indicated by positive and negative values of S, followed by bisection reduction of the separation between the thicknesses until convergence of S to substantially zero or the average value is determined.

A more general list of plots of a parameter vs. wavelength involves selection from the group consisting of:

S=Sin(2Ψ) Sin(Δ);
C=Sin(2Ψ) Cos(Δ);
N=Cos(2Ψ);

vs. thickness and said list of thicknesses is determined by noting where said plot oscillates both positive and negative, and at the first wavelength identified. After determination of the thickness for the influential layer, all parameters in the mathematical model can be allowed to float and a global fit performed.

Note that the mathematical model can include a plurality of surface layers, each of which, except for the most influential layer, is provided fixed values for thickness and optical constants during the determination of the thickness of the most influential layer, but all of which are allowed to float during the global fit.

It is also noted that the mathematical model can include additional parameters corresponding to surface roughness and composition grading, and a plurality of values for at least one selection from the group consisting of:
surface roughness; and
composition grading;

can included to determine if a better fit for thickness can be achieved as evidenced by a lesser square error value.

The method can provide that a polynomial form be selected from the group consisting of:
a cubic spline; and
a basic spline.

The assumed fixed values of optical constants in step b can be only a refractive index and the real and imaginary parts of the optical constants can be related by the Kramers-Kronig relationship.

The present invention will be better understood by reference to the Detailed Description Section of this Specification, in conjunction with the Drawings.

SUMMARY

It is therefore a purpose and/or objective of the disclosed invention to provide a method of obtaining good starting values for parameters in a mathematical model data fitting routine for a most influential layer thickness in a sample.

It is another purpose and/or objective of the disclosed invention to combine said initial value determination with the use of parameterization to fit real and/or imaginary optical constants.

Other purposes and/or objectives will be understood by a reading of the Specification and Claims.

DETAILED DESCRIPTION

Figure 1:
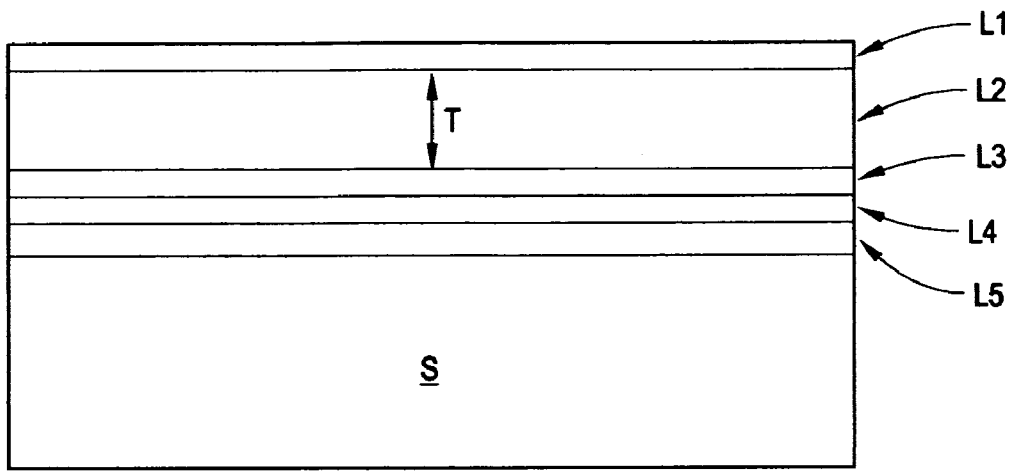
FIG. 1 shows a demonstrative sample comprising a substrate and a plurality of layers on the surface thereof, of which Layer (L2) is demonstrated as the most influential.

Turning now to the Drawings, FIG. 1 shows a demonstrative sample comprising a substrate and a plurality of layers on the surface thereof, of which Layer (L2) is demonstrated as the most influential. This is not necessarily because it has the largest vertical depth as it is the optical thickness that ellipsometry measures, where said optical depth is the product of the index of refraction multiplied by the layer depth (T). A thinner layer could actually be the most influential because of being made of a material with a much higher index of refraction.

As described in the Disclosure of the Invention Section, the present invention method provides that a mathematical model of the Sample be developed which comprises optical constant indicies of refraction and extinction coefficients, (or equivalent dielectric function e1 and e2 values), of Layers (L1) (L3) (L4) (L5) and the Substrate (S). Reasonable values for the index of refraction and extinction coefficient or mathematical equivalents are also fixed for Layer (L2), but the Thickness (T) is allowed to float in a regression procedure which fits the mathematical model to ellipsometric data at a first wavelength. The result is a list of Thickness values (T) which could be valid. The procedure then checks the Thickness (T) values at a second wavelength to determine a Thickness (T) which matches one of those on the list obtained using the first wavelength. With this accomplished the procedure can involve varying the assumed values for the index of refraction and extinction coefficient or mathematical equivalent to see if a better fit results as indicated by a smaller Square Error value between the data and results obtained by calculation using the mathematical model.

Figure 2:
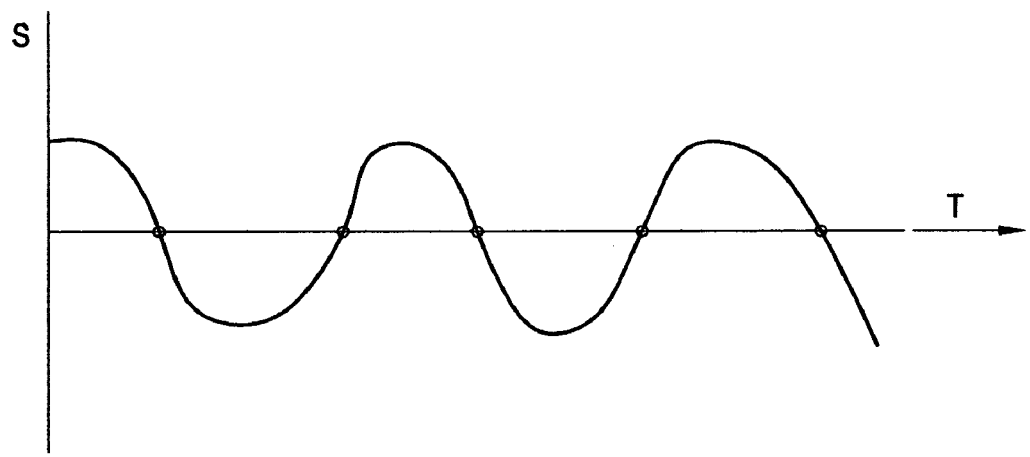
FIG. 2 shows a plot of "S" vs. Thickness of the most influential layer (L2) in FIG. 1.

FIG. 2 shows a plot of "S" vs. Thickness of the most influential layer (L2) in FIG. 1. By using such a plot of "S" obtained at a first wavelength, the list of Thicknesses (T) can be obtained by identifying the zero crossings. Testing said identified values of Thickness (T) at a second, and possibly more, wavelengths will identify which Thickness (T) is the correct one.

Figure 3:
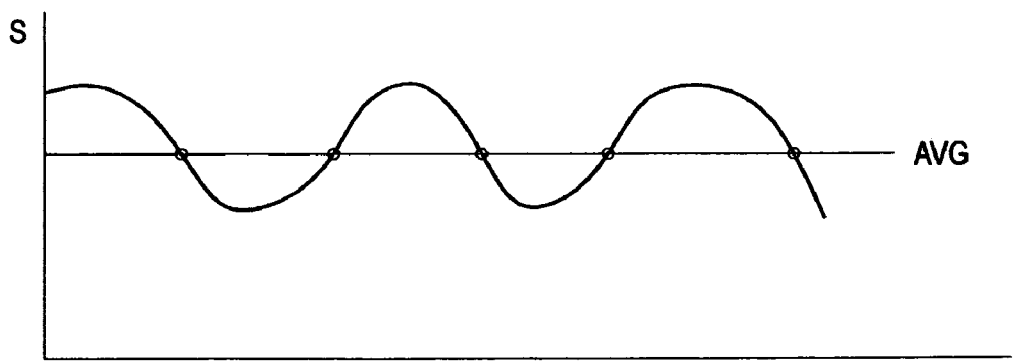
FIG. 3 shows a plot of a parameter "P" vs. Thickness of the most influential layer (L2) in FIG. 1.

FIG. 3 shows a plot of a parameter "P" vs. Thickness of the most influential layer (L2) in FIG. 1. Note the difference in FIG. 3 as compared to FIG. 2 is that the plot of "P" vs. Thickness provides a plurality of average value crossings rather than a plurality of zero crossings.

A spline approach can be applied to model at least a portion of a the real (e1) and/or imaginary (e2) parts of a dielectric function, or the mathematically equivalent refractive index or extinction coefficient. Again, as described in the Disclosure of the Invention Section, the present invention method provides that spline be first fit in a small region, call it (A). Then using the values of coefficients in the spline so determined as starting values, fitting the spline over a larger region (B). Then using the values of coefficients in the spline so determined as starting values, fitting the spline over a larger region (C). Then using the values of coefficients in the spline so determined as starting values, fitting the spline over a larger region (D). The spline can be, for instance, comprised of a number of polynomials, the order of which might change as the method progresses. It must be pointed out that the spline equations between a sequence of "nodes", (eg. between n1(n1') and n2(n2'), or n2(n2') and n3(n3') or n3(n3') and n4(n4')) are different equations with different coefficients. Note, (n1) and (n'1) should be visualized as being spread apart on opposite sides of a central point to form region (A), as are (n2) and (n2') with a larger spread therebetween to form region (B) etc. Further, the spline equations can be Basic-Spline (B-Spline) or what will be termed Ordinary-Spline herein. In the B-Spline case the influence of the values of coefficients for a spline equation between say nodes n3 and n4 becomes more and more insignificant the further from that interval one moves. That is, the equation coefficient values for an equation in the interval n2-n3 will have some influence over equation coefficient values in the region n3-n4, but substantially no effect on the coefficient values in interval n3'-n4'. Under the Ordinary-Spline approach this is not the case. A change in a equation coefficient values in interval n3-n4 can have a significant effect on coefficient values in interval n3'-n4', for instance. Both Spline approaches are described in a book tiled "Numerical Mathematics and Computing" by Cheney and Kincaid, Third Edition, Brooks/Cole Publishing Company, 1994 and the teachings therein are incorporated by reference herein.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of determining an initial thickness of the most influential surface layer in a sample which comprises a substrate and at least one layer on a surface thereof, by the steps of:

practicing steps a and b in either order or simultaneously:
a) obtaining ellipsometric data over spectroscopic range of wavelengths by causing a spectroscopic polarized beam of electromagnetic radiation to interact with said sample and enter a detector;
b) proposing a mathematical model of said sample including a variable thickness parameter for the most influential surface layer, and an assumed reasonable values of optical constants therefore;
c) selecting a first wavelength and determining a list of most influential layer thicknesses for which the mathematical model provides a match to the data at that wavelength, in view of said assumed reasonable values of optical constants for said most influential layer;
d) sequentially testing each thickness for the most influential layer on the list at least one additional wavelength to determine the thickness on the list for which the mathematical model provides a best-fit match to the ellipsometric data at said at least one additional wavelength.

2. A method as in claim 1 in which step d involves determining which thickness on the list provides a match to the ellipsometric data at a plurality of additional wavelengths.

3. A method as in claim 2 wherein, after step d, a global fit at all wavelengths is performed to better identify thickness and optical constants of said most influential layer.

4. A method as in claim 1 which further involves testing a plurality of optical constant values around said reasonable optical constant values to determine if a better fit for thickness can be achieved as evidenced by a lesser square error value, said optical constant values being varied for at least one optical constant selected from the group consisting of:
the real; and
the imaginary;
part.

5. A method as in claim 4 wherein, after step d, a global fit at all wavelengths is performed to better identify thickness and optical constants of said most influential layer.

6. A method as in claim 1 wherein, after step d, a global fit at all wavelengths is performed to better identify thickness and optical constants of said most influential layer.

7. A method as in claim 1, in which the ellipsometric data is presented in the form of:
$S=\mathrm{Sin}(2\Psi)\,\mathrm{Sin}(\Delta)$ vs. thickness;
which oscillates both negative and positive about a zero at said first wavelength wherein the list of thicknesses is determined by noting a plurality of locations where the S value crosses said zero.

8. A method as in claim 7, in which thicknesses is determined by noting thicknesses before and after the thickness at which the S value passes through a zero, as indicated by positive and negative values of S, followed by bisection reduction of the separation between the thicknesses until convergence of S to substantially zero is determined.

9. A method as in claim 1 in which the ellipsometric data is presented in a form which oscillates both negative and positive about an average value, instead of a zero value.

10. A method as in claim 1, in which the ellipsometric data is presented in the form of:
S=Sin(2Ψ) Sin(Δ) vs. thickness;
which oscillates both negative and positive about said average value at said first wavelength wherein the list of thicknesses is determined by noting a plurality of locations where the S value crosses said zero.

11. A method as in claim 10, in which thicknesses is determined by noting thicknesses before and after the thickness at which the S value passes through said average value, as indicated by positive and negative values of S, followed by bisection reduction of the separation between the thicknesses until convergence of S to substantially said average value is determined.

12. A method as in claim 1 wherein a plot of a parameter vs. wavelength is selected from the group consisting of:
S=Sin(2Ψ) Sin(Δ);
C=Sin(2Ψ) Cos(Δ);
N=Cos(2Ψ);
vs. thickness and said list of thicknesses is determined by noting where said plot oscillates both positive and negative, and at the first wavelength identified.

13. A method as in claim 1, wherein the mathematical model includes additional parameters corresponding to surface roughness and composition grading;
and a plurality of values for at least one selection from the group consisting of:
surface roughness; and
composition grading;
are substituted to determine if a better fit for thickness can be achieved as evidenced by a lesser square error value.

14. A method as in claim 1, wherein the mathematical model includes a plurality of surface layers, each of which, except for the most influential layer, is provided fixed values for thickness and optical constants.

15. A method as in claim 1 in which the assumed fixed values of optical constants in step b involves only a refractive index.

16. A method as in claim 1 in which the assumed fixed values of optical constants in step b involves at least one selection from the group consisting of:
real refractive index (n);
imaginary extinction coefficient (k);
real part of dielectric function (e1); and
imaginary part of dielectric function (e2).

17. A method as in claim 16 in which the real and imaginary parts of the optical constant are selected and related by the Kramers-Kronig relationship.

18. A method as in claim 17 in which the real and imaginary parts of the optical constant are related by the Kramers-Kronig relationship.

19. A method of fitting a mathematical model to ellipsometric data comprising the steps of:
a) obtaining ellipsometric data over a spectroscopic range;
b) proposing a mathematical model comprising real and imaginary parts of optical constants as well as layer thicknesses;
c) selecting a subset of said ellipsometric data and evaluating coefficients in polynomials in said mathematical model which are used to represent at least one of the real and imaginary parts of optical constants, as well said layer thicknesses;
d) increasing the subset of the data being considered, and using the values obtained in step c as starting values, evaluating values for polynomial coefficients in the mathematical model comprising real and imaginary parts of optical constants, as well other mathematical model parameters in the entire selected subset of data.

20. A method as in claim 19, in which the subset of the data being considered is again increased, and using the values obtained in step d as starting values, evaluating values for polynomial coefficients in the mathematical model comprising real and imaginary parts of optical constants, as well other mathematical model parameters in the entire selected subset of data.

21. A method as in claim 20 in which the polynomial form is selected from the group consisting of:
a cubic spline; and
a basic spline.

22. A method as in claim 19 in which the polynomial form is selected from the group consisting of:
a cubic spline; and
a basic spline.

23. A method of fitting ellipsometric data to a mathematical model comprising:
A) determining an initial thickness of the most influential surface layer in a sample which comprises a substrate and at least one layer on a surface thereof, by the steps of:
practicing steps a and b in either order or simultaneously:
a) obtaining ellipsometric data over spectroscopic range of wavelengths by causing a spectroscopic polarized beam of electromagnetic radiation to interact with said sample and enter a detector;
b) proposing a mathematical model of said sample including a variable thickness parameter for the most influential surface layer, and an assumed reasonable value of optical constants therefore;
c) selecting a first wavelength and determining a list of most influential layer thicknesses for which the mathematical model provides a match to the data at that wavelength, in view of said assumed reasonable values of optical constants for said most influential layer;
d) sequentially testing each thickness for the most influential layer on the list at least one additional wavelength to determine the thickness on the list for which the mathematical model provides a match to the ellipsometric data at said at least one additional wavelength; and
B) utilizing said identified thickness for the most influential layer as a starting value and performing a fitting procedure to better define said most influential layer comprising the step of:
e) selecting a subset of said ellipsometric data and assigning a polynomial to represent at least one of the real and imaginary parts of the optical constants and evaluating coefficients in said polynomial in said mathematical model, as well as re-evaluating said most influential layer thickness by a fitting procedure to said subset of data.

24. A method of fitting data as in claim 23 which further comprises an additional step:
f) increasing the subset of the data being considered, and using the values obtained in step c as starting values, evaluating values for polynomial coefficients in the mathematical model which represent at least one of said real and imaginary parts of the optical constants, as well as re-evaluating the thickness of the most influential layer over the entire selected subset of data.

25. A method as in claim 24 wherein, after step d, a global fit at all wavelengths is performed to better identify thickness and optical constant values of said most influential layer.

26. A method as in claim 24 in which the polynomial form is selected from the group consisting of:
   a cubic spline; and
   a basic spline.

27. A method as in claim 23 in which the determination of which thickness on the list provides a match to the ellipsometric data at a plurality of additional wavelengths.

28. A method as in claim 23 which further involves testing a plurality of optical constant values around said reasonable optical constant values to determine if a better fit for thickness can be achieved as evidenced by a lesser square error value, said optical constant values being varied for at least one optical constant selected from the group consisting of:
   the real; and
   the imaginary;
part.

29. A method as in claim 23 wherein, after step d, a global fit at all wavelengths is performed to better identify thickness and optical constant values of said most influential layer.

30. A method as in claim 23, in which the ellipsometric data is presented in the form of:
   S=Sin(2Ψ) Sin(ΔA) vs. thickness;
which oscillates both negative and positive about a zero at said first wavelength wherein the list of thicknesses is determined by noting a plurality of locations where the S value crosses said zero.

31. A method as in claim 30, in which thicknesses is determined by noting thicknesses before and after the thickness at which the S value passes through a zero, as indicated by positive and negative values of S, followed by bisection reduction of the separation between the thicknesses until convergence of S to substantially zero is determined.

32. A method as in claim 23 in which the ellipsometric data is presented in a form which oscillates both negative and positive about an average value, instead of a zero value.

33. A method as in claim 23, in which the ellipsometric data is presented in the form of:
   S=Sin(2Ψ) Sin(Δ) vs. thickness;
which oscillates both negative and positive about said average value at said first wavelength wherein the list of thicknesses is determined by noting a plurality of locations where the S value crosses said zero.

34. A method as in claim 33, in which thicknesses is determined by noting thicknesses before and after the thickness at which the S value passes through said average value, as indicated by positive and negative values of S, followed by bisection reduction of the separation between the thicknesses until convergence of S to substantially said average value is determined.

35. A method as in claim 23 wherein a plot of a parameter vs. wavelength is selected from the group consisting of:
   S=Sin(2Ψ) Sin(Δ);
   C=Sin(2Ψ) Cos(Δ);
   N=Cos(2Ψ);
vs. thickness and said list of thicknesses is determined by noting where said plot oscillates both positive and negative, and at the first wavelength identified.

36. A method as in claim 23, wherein the mathematical model includes a plurality of surface layers, each of which, except for the most influential layer, is provided fixed values for thickness and optical constants.

37. A method as in claim 23, wherein the mathematical model includes additional parameters corresponding to surface roughness and composition grading;
   and a plurality of values for at least one selection from the group consisting of:
      surface roughness; and
      composition grading;
   are substituted to determine if a better fit for thickness can be achieved as evidenced by a lesser square error value.

38. A method as in claim 23 in which the polynomial form is selected from the group consisting of:
   a cubic spline; and
   a basic spline.

39. A method as in claim 23 in which the assumed fixed values of optical constants in step b involves only a refractive index.

40. A method as in claim 23 in which the assumed fixed values of optical constants in step b involves at least one selection from the group consisting of:
   real refractive index (n);
   imaginary extinction coefficient (k);
   real part of dielectric function (e1); and
   imaginary part of dielectric function (e2).

* * * * *

UNITED STATES PATENT AND TRADEMARK OFFICE
CERTIFICATE OF CORRECTION

PATENT NO. : 7,362,435 B1  Page 1 of 1
APPLICATION NO. : 11/326060
DATED : April 22, 2008
INVENTOR(S) : Jobe et al.

It is certified that error appears in the above-identified patent and that said Letters Patent is hereby corrected as shown below:

Title page, item (73) Assignee: Delete "Wollam" and replace with --Woollam--.

Signed and Sealed this

First Day of July, 2008

JON W. DUDAS
*Director of the United States Patent and Trademark Office*